(12) United States Patent
Ciulla et al.

(10) Patent No.: US 10,603,030 B2
(45) Date of Patent: Mar. 31, 2020

(54) ADJUSTABLE IMPLANTS AND METHODS OF IMPLANTING THE SAME

(71) Applicant: Boston Scientific Scimed, Inc., Maple Grove, MN (US)

(72) Inventors: Ronald Ciulla, Westford, MA (US); James M. Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 6 days.

(21) Appl. No.: 15/842,156

(22) Filed: Dec. 14, 2017

(65) Prior Publication Data
US 2018/0103945 A1  Apr. 19, 2018

Related U.S. Application Data

(63) Continuation of application No. 14/195,599, filed on Mar. 3, 2014, now abandoned.
(Continued)

(51) Int. Cl.
*A61B 17/04* (2006.01)
*A61F 2/00* (2006.01)
*A61B 17/00* (2006.01)

(52) U.S. Cl.
CPC ........ *A61B 17/0401* (2013.01); *A61F 2/0045* (2013.01); *A61B 2017/00805* (2013.01);
(Continued)

(58) Field of Classification Search
CPC ........ A61B 17/0401; A61B 2017/0412; A61B 2017/044; A61B 2017/0453;
(Continued)

(56) References Cited

U.S. PATENT DOCUMENTS 6,019,762 A * 2/2000 Cole ................. A61B 17/8047
606/104
6,149,653 A  11/2000 Deslauriers
(Continued)

FOREIGN PATENT DOCUMENTS

EP       596829 A1    5/1994
WO    2009055800 A1   4/2009
(Continued)

OTHER PUBLICATIONS

Invitation to Pay Add'l Fees and Partial Search Report for PCT Application No. PCT/US14/20383, dated Jul. 15, 2014, 6 pages.
(Continued)

*Primary Examiner* — Kaylee R Wilson
(74) *Attorney, Agent, or Firm* — Brake Hughes Bellermann LLP (57) ABSTRACT

In one embodiment, a medical device includes a tissue anchor has a first portion and a second portion. The tissue anchor is configured to be placed within bodily tissue of a patient. The first portion of the tissue anchor includes an extension member configured to engage the bodily tissue to help retain the tissue anchor within the bodily tissue. The first portion has an inner surface and defines a cavity. The second portion of the tissue anchor has a helical ridge. The helical ridge is configured to engage the inner surface of the first portion of the tissue anchor to movably couple the second portion of the tissue anchor to the first portion of the tissue anchor.

5 Claims, 7 Drawing Sheets

Related U.S. Application Data (60) Provisional application No. 61/775,079, filed on Mar. 8, 2013.

(52) U.S. Cl.
CPC ... *A61B 2017/044* (2013.01); *A61B 2017/045* (2013.01); *A61B 2017/0412* (2013.01); *A61B 2017/0414* (2013.01); *A61B 2017/0417* (2013.01); *A61B 2017/0453* (2013.01); *A61B 2017/0464* (2013.01)

(58) Field of Classification Search
CPC ...... A61B 2017/045; A61B 2017/0417; A61B 2017/0414; A61B 2017/00805; A61F 2/0045
See application file for complete search history.

(56) References Cited

U.S. PATENT DOCUMENTS

| | | | |
|---|---|---|---|
| 6,162,234 A | 12/2000 | Freedland et al. | |
| 2006/0265042 A1 | 11/2006 | Catanese et al. | |
| 2007/0005068 A1 | 1/2007 | Sklar | |
| 2007/0021649 A1 | 1/2007 | Nowlin et al. | |
| 2008/0281353 A1* | 11/2008 | Aranyi | A61B 17/064 606/219 |
| 2009/0112270 A1 | 4/2009 | Lunn et al. | |
| 2009/0157124 A1 | 6/2009 | Ferragamo et al. | |
| 2010/0106254 A1* | 4/2010 | DelSignore | A61B 17/0401 623/21.15 |
| 2010/0191045 A1 | 7/2010 | Gobron et al. | |
| 2010/0197998 A1 | 8/2010 | Comiter et al. | |
| 2010/0262185 A1 | 10/2010 | Gelfand et al. | |
| 2010/0292731 A1 | 11/2010 | Gittings et al. | |
| 2011/0112576 A1 | 5/2011 | Nguyen et al. | |
| 2012/0035627 A1* | 2/2012 | Ostrovsky | A61B 17/0401 606/151 |
| 2013/0006302 A1* | 1/2013 | Paulk | A61B 17/0401 606/232 |
| 2014/0257026 A1 | 9/2014 | Ciulla et al. | |

FOREIGN PATENT DOCUMENTS

| | | |
|---|---|---|
| WO | 2011060022 A2 | 5/2011 |
| WO | 2014138104 A2 | 9/2014 |
| WO | 2014138104 A3 | 11/2014 |

OTHER PUBLICATIONS

International Preliminary Report on Patentability for PCT Application No. PCT/US14/20383, dated Sep. 17, 2015, 11 pages.
International Search Report and Written Opinion for PCT Application No. PCT/US14/20383, dated Sep. 30, 2014, 17 pages.

* cited by examiner

ADJUSTABLE IMPLANTS AND METHODS OF IMPLANTING THE SAME

CROSS-REFERENCE TO RELATED APPLICATIONS

This application is a Continuation of, and claims priority to, U.S. patent application Ser. No. 14/195,599, filed on Mar. 3, 2014, entitled "ADJUSTABLE IMPLANTS AND METHODS OF IMPLANTING THE SAME", which, in turn, claims priority to U.S. Patent Application No. 61/775,079, filed on Mar. 8, 2013, entitled "ADJUSTABLE IMPLANTS AND METHODS OF IMPLANTING THE SAME", the disclosures of which are incorporated by reference herein in their entirety.

TECHNICAL FIELD

This disclosure relates generally to medical devices and more particularly to implants configured to provide support within a body of a patient and methods for securing such implants with the body of the patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse. Additionally, some medical procedures are performed to treat various male pelvic dysfunctions, such as urinary incontinence.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension of a portion of a body of a patient. For example, a hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of anchors disposed at various fixation points.

It may be difficult to insert known implants and apply the correct tension to the known implants during the implantation procedure. Thus, it would be beneficial to provide an implant and system that facilitates the implantation of the implant and the tensioning of the implant during the implantation procedure. It would also be beneficial to provide an implant and system that that facilitates the adjustment of the effective length, such as the length between the anchors, of an implant.

SUMMARY

In one embodiment, a medical device includes a tissue anchor has a first portion and a second portion. The tissue anchor is configured to be placed within bodily tissue of a patient. The first portion of the tissue anchor includes an extension member configured to engage the bodily tissue to help retain the tissue anchor within the bodily tissue. The first portion having an inner surface and defining a cavity. The second portion of the tissue anchor has a helical ridge. The helical ridge is configured to engage the inner surface of the first portion of the tissue anchor to movably couple the second portion of the tissue anchor to the first portion of the tissue anchor. Accordingly, the medical device is a medical device that includes a size or a length that can be adjusted.

In another embodiment, a medical device includes an elongate member, a shaft member, and an actuator. The elongate member has a proximal end portion and a distal end portion. The elongate member defines a cavity. The shaft member is at least partially disposed within the cavity of the elongate member. The shaft member is configured to rotate with respect to the elongate member. The actuator is operatively coupled to the shaft member and is configured to cause the shaft member to rotate with respect to the elongate member. Accordingly, the medical device is a medical device that includes a size or a length that can be adjusted.

In yet another embodiment, a method of placing a medical device within a body of a patient includes inserting a tissue anchor into the body of the patient, the tissue anchor having a first portion and second portion; and rotating the second portion of the tissue anchor with respect to the first portion of the tissue anchor.

The details of one or more implementations are set forth in the accompanying drawings and the description below. Other features will be apparent from the description and drawings, and from the claims.

DETAILED DESCRIPTION

The devices and methods described herein are generally directed to implants configured to be disposed within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient. The implants and procedures described herein may be used in a female patient or a male patient.

An implant according to an embodiment of the invention can be implanted, for example, through a vaginal incision, in a retro-pubic direction (behind the pubic bone), in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

Various embodiments of implants are described herein. The implants can be delivered to various parts of the body of the patient using a variety of different method and delivery devices. The implants and methods disclosed herein include pelvic floor implants, but the implants may be configured to be placed and methods may be used to place such implants in any portion of the body of the patient.

An implant can be delivered to a pelvic region of a patient using a variety of different delivery devices, only some examples of which are described herein.

Figure 1:
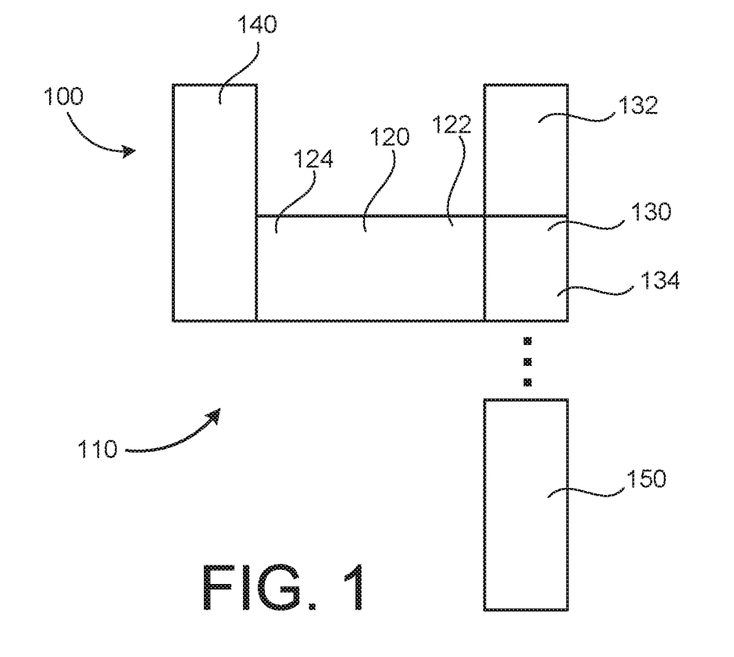
FIG. 1 is a schematic illustration of a medical device according to an embodiment of the invention.

FIG. 1 is a schematic illustration of a medical device or system 100. The medical device 100 includes an implant 110 and an insertion tool 150. The implant 110 has a support member 120. The support member 120 includes a first end portion 122 coupled to a first mesh carrier or anchor 130 and a second end portion 124 coupled to a second mesh carrier or anchor 140.

The implant 110 is configured to be placed within a body of a patient to provide support to a portion of the body of the patient. For example, in some embodiments, the support member 120 of the implant 110 is configured to be placed proximate or adjacent a bladder of a patient to provide support to the bladder of the patient. In other embodiments, the support member 120 of the implant is configured to support the urethera or bladder neck of a patient. In yet other embodiments, the support member 120 of the implant 110 is configured to be placed adjacent another portion of the body to provide support to another portion of the body.

The support member includes end portions 122 and 124. The implant 110 also includes mesh carriers or anchors 130 and 140 coupled to end portions 122 and 124 of the support member 120. In some embodiments, the anchors 130 and 140 are directly coupled to the end portions 122 and 124 of the support member 120. In other embodiments, a tether or suture is coupled between the end portions 122 and 124 and the anchors 130 and 140. Any known mechanism may be used to couple the anchors 130 and 140 to the support member 120. For example, an adhesive may be used to couple the anchors 130 and 140 to the support member 120. Alternatively, the anchors 130 and 140 may surround and be frictionally coupled to the support member 120.

The anchors 130 and 140 are configured to be disposed in bodily tissue and provide a support for implant 110. Specifically, once disposed within bodily tissue, the anchors 130 and 140 are configured to help retain the implant 110 in place within a body of a patient. In some embodiments, the anchors 130 and 140 are configured to be disposed within pelvic tissue of a patient. In other embodiments, the anchors 130 and 140 are configured to be disposed in other bodily tissue, such as muscle tissue.

In some embodiments, the anchors 130 and 140 include barbs or projections that are configured to help secure the anchors 130 and 140 in place within the bodily tissue. In some embodiments, the anchors 130 and 140 do not include any sort of structure for securing the anchors in place within the body of the patient.

In the illustrated embodiment, the anchor 130 includes a first portion 132 and a second portion 134. The first end portion 122 of the support member 120 is coupled to the second portion 134 of the anchor 130. The second portion 134 of the anchor 130 is configured to move with respect to the first portion 132 of the anchor 130. For example, in some embodiments, the second portion 134 of the anchor 130 is configured to selectively move with respect to the first portion 132 of the anchor 130. In such an embodiment, the second portion 134 can be moved with respect to the first portion 132 of the anchor 130 to a desired location and then locked or fixed with respect to the first portion 132 of the anchor 130 (to no longer move with respect to the first portion 132 of the anchor 130). In some embodiments, the second portion 134 of the anchor 130 is configured to rotate with respect to the first portion 132 of the anchor 130. In some such embodiments, the second portion 134 of the anchor 130 moves with respect to the first portion 132 of the anchor 130 is a screw type manner. In other embodiments, the second portion of the anchor is configured to be selectively coupled to the first portion of the anchor via a different mechanism. For example, in some embodiments, the second portion may be configured to be frictionally fit or coupled to the first portion. In other embodiments, tapered surfaces or clamping mechanisms may be used to selectively or movably couple the second portion of the anchor to the first portion of the anchor.

In some embodiments, the anchor 130 may be disposed within the body of the patient. For example, the anchor may be placed within in bodily tissue such that a barb or other projection of the anchor 130 (such as a barb or other projection disposed on or extending from the first portion 132 of the anchor 130) engages body tissue to couple the anchor 130 to the bodily tissue. The tension or location of the implant 110 may then be adjusted by moving the second portion 134 with respect to the first portion 132 of the anchor 130.

In some embodiments, the anchor 140 is a two part anchor (similar to anchor 130). In other embodiments, the anchor 140 is a one part anchor (or an anchor that does not include any portions that are configured to move with respect to each other).

The insertion tool 150 of the medical device 100 is configured to place the implant 110 into the body of the patient. For example, in some embodiments, the insertion tool 150 is configured to engage the implant 110 and guide the implant into position within the body of the patient. In some embodiments, the insertion tool 150 is configured to engage the second portion 134 of the anchor 130 to deliver or guide the anchor 130 into place within the body of the patient. In some embodiments, the insertion tool 150 is configured to cause the second portion 134 of the anchor 130 to move with respect to the first portion 132 of the anchor 130. Similarly, the insertion tool 150 may be used to place the second anchor 140 into the body of the patient.

For example, in embodiments where the implant 110 is being placed in a pelvic region of a female patient, a vaginal incision may be made and the implant 110 may be placed into the body of the patient through the vaginal incision. In some embodiments, the insertion tool 150 may be used to guide the implant 110 into the vaginal incision and to the appropriate location within the body of the patient. In other embodiments, the implant 110 is inserted into the body of the patient through a different bodily incision and the anchors 130 and 140 are placed using a different type of insertion tool.

The implant 110, including the support member 120, may be formed of any biocompatible material. In some embodiments, the support member 120 is formed of a mesh material. For example, the support member 120 may be formed of Advantage® mesh or the Polyform™ synthetic mesh, both as sold by Boston Scientific Corporation. In some embodiments, in the support member 120 may be formed of a polymer material. In some embodiments, the material of the support member 120 allows for tissue in-growth to secure the implant 100 to the bodily tissue of the patient. In some embodiments, the mesh weight can be approximately between 15 g/cm² to 35 g/cm² (e.g., 20 g/cm², 25 g/cm², 30 g/cm²). In other embodiments, the mesh weight can be greater than 35 g/cm².

In some embodiments, the support member 120 includes tangs to help retain the implant in place within the body of the patient. In such embodiments, the tang or tangs are configured to engage the bodily tissue surrounding the support member 120 help retain the implant 100 in place within the body of the patient. The terms "tanged" or "tangs" as used herein mean roughened or jagged edges or areas, such as can result from cutting a woven or knit mesh material.

The anchors 130 and 140 may be formed of any biocompatible material. For example, in some embodiments, the anchors 130 and 140 are formed of polypropylene or a bio-absorbable material.

Figure 2:
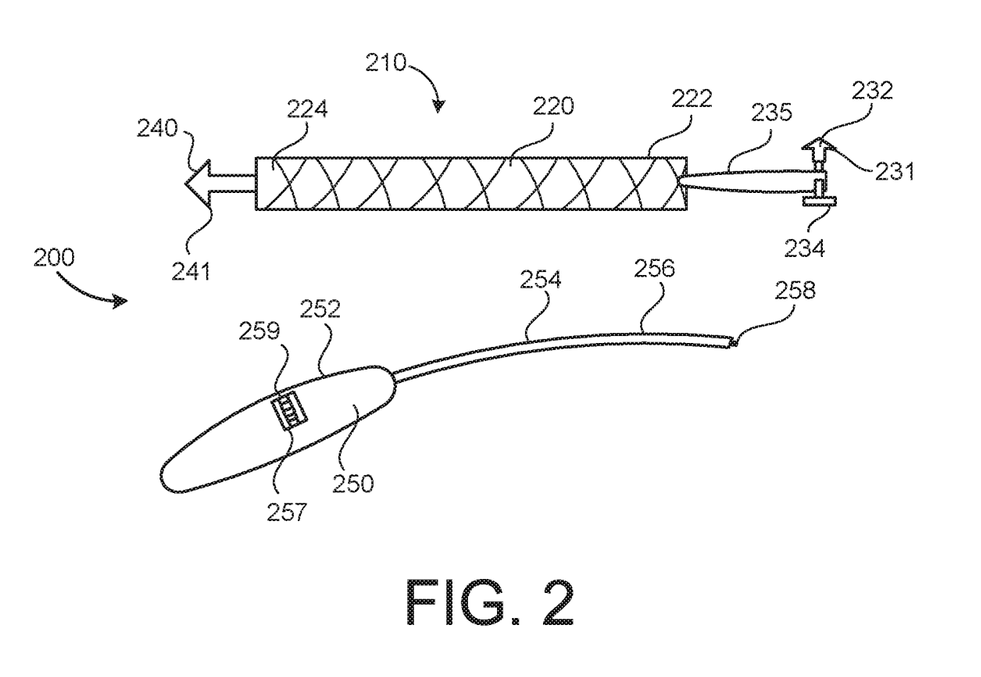
FIG. 2 is a top view of a medical device according to an embodiment of the invention.

FIG. 2 illustrates a medical device or system 200 according to an embodiment. The medical device 200 includes an implant 210 and an insertion tool 250. The implant 210 has a support member 220. The support member 220 includes a first end portion 222 coupled to a first mesh carrier or anchor 230 and a second end portion 224 coupled to a second mesh carrier or anchor 240.

The implant 210 is configured to be placed within a body of a patient to provide support to a portion of the body of the patient. For example, in some embodiments, the support member 220 of the implant 210 is configured to be placed proximate or adjacent a bladder of a patient to provide support to the bladder of the patient. In other embodiments, the support member 220 of the implant is configured to support the urethera or bladder neck of a patient. In yet other embodiments, the support member 220 of the implant 210 is configured to be placed adjacent another portion of the body to provide support to another portion of the body.

The support member includes end portions 222 and 224. The implant 210 also includes mesh carriers or anchors 230 and 240. Anchor 230 is coupled to end portion 222 and anchor 240 is coupled to the end portion 224. In some embodiments, the anchors 230 and 240 are directly coupled to the end portions 222 and 224 of the support member 220. In the illustrated embodiment, a tether or suture 235 is coupled between the end portions 222 and the anchors 230. The tether or suture 235 is looped or threaded through the support member 220 and is looped around and tied to the anchor 230. Any other known mechanisms may be used to couple the anchors 230 and 240 to the support member 220. For example, an adhesive may be used to couple the anchors 230 and 240 to the support member 220. Alternatively, the end portions 222 and 224 may surround and be frictionally coupled to the anchors 230 and 240.

The anchor 230 and 240 are configured to be disposed in bodily tissue and provide a support for implant 210. Specifically, once disposed within bodily tissue, the anchors 230 and 240 are configured to help retain the implant 210 in place within a body of a patient. In some embodiments, the anchors 230 and 240 are configured to be disposed within pelvic tissue of a patient. In other embodiments, the anchors 230 and 240 are configured to be disposed in other bodily tissue, such as muscle tissue.

In the illustrated embodiment, the anchor 230 includes a barb or projection 231 disposed on or projecting from the first portion of the anchor 232. The anchor 240 includes also includes a barb or projection 241 projecting from the anchor 240. In other embodiments, the anchors 230 and 240 do not include any barbs or projections for securing the anchors 230 and 240 in place within the body of the patient.

Figure 3:
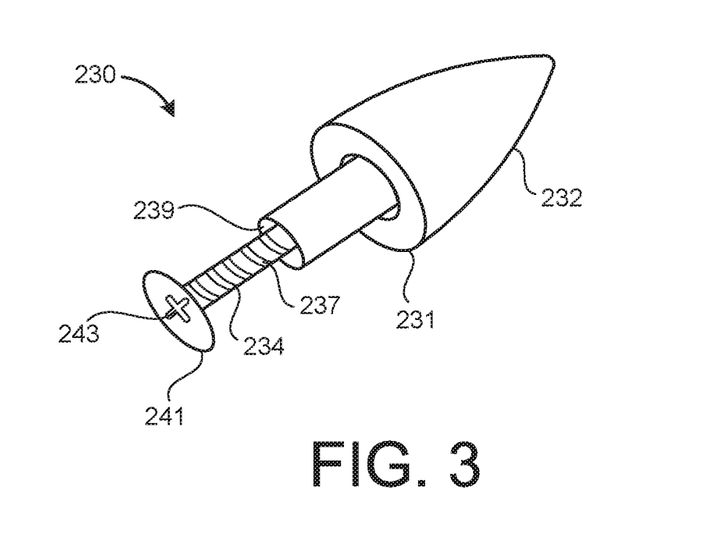
FIG. 3 is a perspective view of an anchor of the medical device of FIG. 2.
Figure 4:
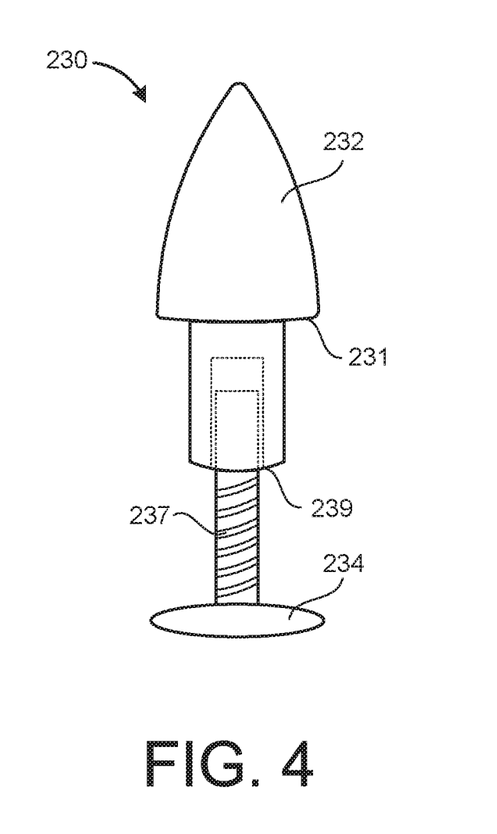
FIG. 4 is a side view of the anchor of FIG. 3.
Figure 5:
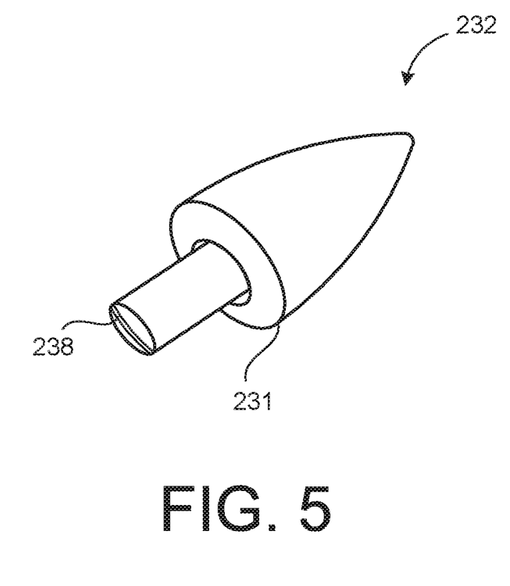
FIG. 5 is a perspective view of a first portion of the anchor of FIG. 3.
Figure 6:
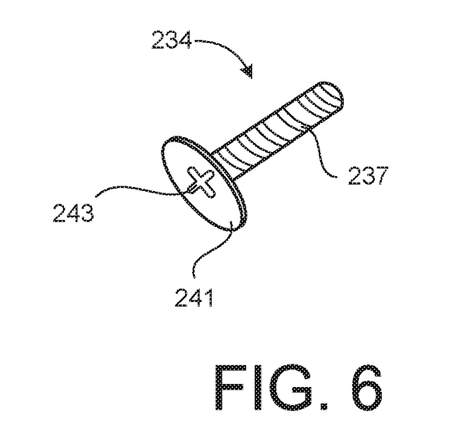
FIG. 6 is a perspective view of the second portion of the anchor of FIG. 3.

In the illustrated embodiment, the anchor 230 includes a first portion 232 and a second portion 234. FIG. 3 is a perspective view of the anchor 230. FIG. 4 is a side view of the anchor 230. FIG. 5 is a perspective view of the first portion 232 of the anchor 230. FIG. 6 is a perspective view of the second portion 234 of the anchor 230. The first end portion 222 of the support member 220 is coupled to the second portion 234 of the anchor 230 (as described above). The second portion 234 of the anchor 230 is configured to move with respect to the first portion 232 of the anchor 230. In the illustrated embodiment, the second portion 234 of the anchor 230 moves with respect to the first portion 232 of the anchor 230 as a screw moves. The second portion 234 of the anchor 230 includes a ridge (a helical ridge) 237. The first portion 232 of the anchor 230 defines a lumen 239. The lumen 239 is configured to receive the first portion 232 of the anchor 230 and has a sidewall that defines a groove (a helical groove) 238. The helical groove 238 is configured to receive the helical ridge 237 of the second portion 234 of the anchor 230. The helical groove 238 and the helical ridge 237 interact to selectively move the second portion 234 of the anchor 230 with respect to the first portion 232 of the anchor 230. Specifically, the second portion 234 of the anchor 230 may be rotated with respect to the first portion 232 of the anchor 230 to move the second portion 234 longitudinally with respect to the first portion 232 of the anchor 230.

In the illustrated embodiment, a proximal end 241 of the second portion 234 of the anchor 230 defines a recess or slot 243. The recess 243 is configured to receive a portion of the delivery tool 250 to allow for the coupling or engaging of the delivery tool 250 with the anchor 230 and to allow for the rotation of the second portion 234 of the anchor 230 with respect to the first portion 232 of the anchor 230. In the illustrated embodiment, the recess 243 is star or "t" shaped. In other embodiments, the recess 243 has a different shape.

In some embodiments, the anchor 230 may be disposed within the body of the patient. For example, the anchor may be placed within in bodily tissue such that the barb or projection 231 of the anchor 230 engages body tissue to couple the anchor 230 to the bodily tissue. The tension of the implant 210 (or the location of the support member 220) may then be adjusted by moving the second portion 234 with respect to the first portion 232 of the anchor 230.

In the illustrated embodiment, the second anchor 240 is a one part anchor (or an anchor that does not include any portions that are configured to move with respect to each other). In other embodiments, the second anchor 240 is a two part anchor and is structurally and functionally similar to the first anchor 230.

The implant 210, including the support member 220, may be formed of any biocompatible material. In some embodiments, the support member 220 is formed of a mesh material. For example, the support member 220 may be formed of Advantage® mesh or the Polyform™ synthetic mesh, both as sold by Boston Scientific Corporation. In some embodiments, in the support member 220 may be formed of a polymer material. In some embodiments, the material of the support member 220 allows for tissue in-growth to secure the implant 200 to the bodily tissue of the patient.

In some embodiments, the support member 220 includes tangs to help retain the implant in place within the body of the patient. In such embodiments, the tang or tangs are configured to engage the bodily tissue surrounding the support member 220 help retain the implant 200 in place within the body of the patient. The terms "tanged" or "tangs" as used herein mean roughened or jagged edges or areas, such as can result from cutting a woven or knit mesh material.

Figure 7:
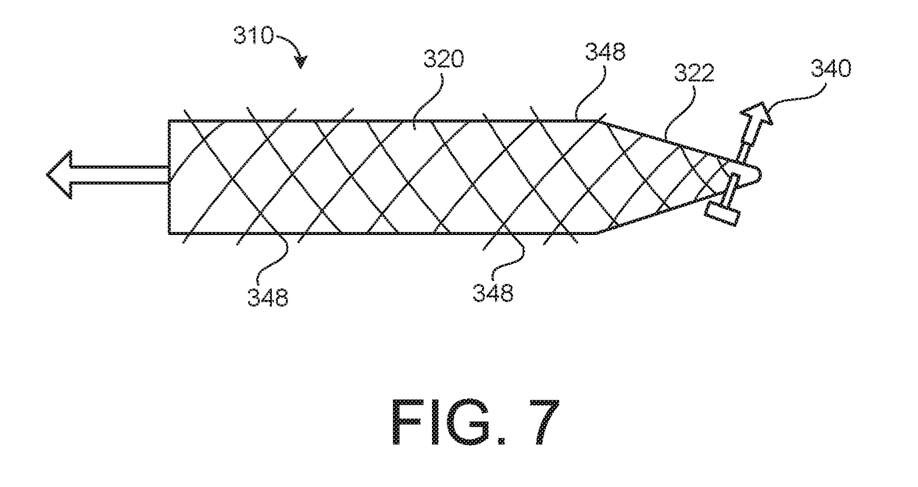
FIG. 7 is a top view of an implant according to an embodiment of the invention.

FIG. 7 is a top view of an implant 310 according to another embodiment. The implant 320 includes tangs or projections 348 that extend from the support member 320 of the implant (such as the rough or jagged edges of a cut mesh material). In some embodiments, the tangs 348 are configured to engage bodily tissue when the implant 310 is disposed within the body to help retain the implant 310 in place within the body of the patient.

The support member 320 of the implant 310 includes a tapered end portion 322. The tapered end portion 322 is directly coupled to the anchor 330. In the illustrated embodiment, the anchor 330 extends through a portion of the tapered end portion 322 to couple the anchor 330 to the tapered end portion 322. In other embodiments, the tapered end portion 322 is coupled to the anchor 330 via another mechanism, such an adhesive or other mechanism.

The insertion tool 250 of the medical device 200 is configured to place the implant 210 into the body of the patient. For example, in some embodiments, the insertion tool 250 is configured to engage the implant 210 and guide the implant into position within the body of the patient.

Figure 8:
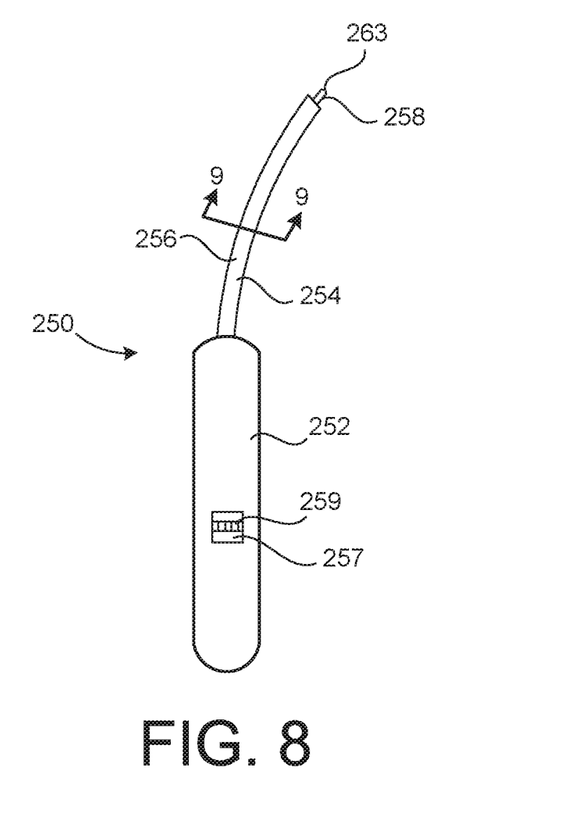
FIG. 8 is a side view of an insertion tool of the medical device of FIG. 2.
Figure 9:
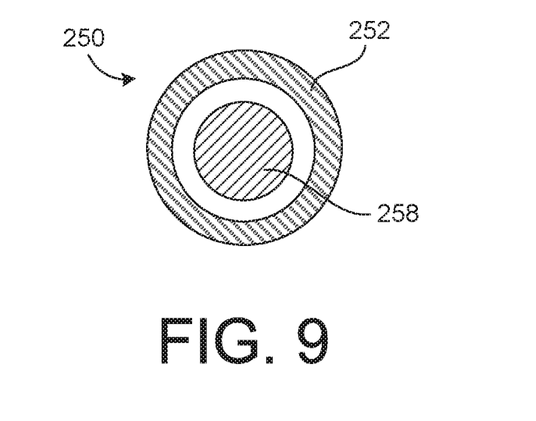
FIG. 9 is a cross-sectional view of the insertion tool taken along line 9-9 of FIG. 8.
Figure 10:
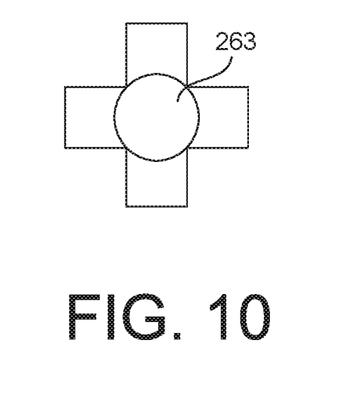
FIG. 10 is a distal end view of the insertion tool of FIG. 8
Figure 11:
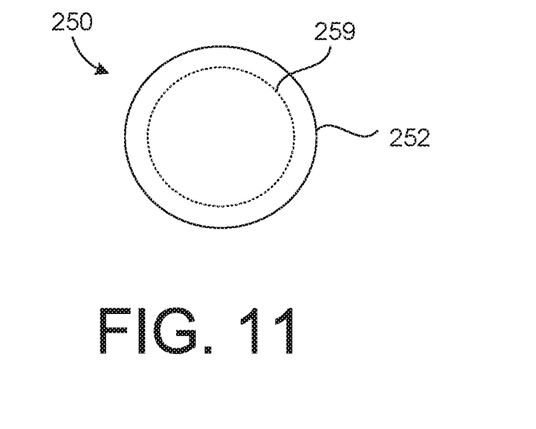
FIG. 11 is a proximal end view of the insertion tool of FIG. 8.

FIG. 8 is a side view of the insertion tool 250. FIG. 9 is a cross-sectional view of the insertion tool 250 taken along line 9-9 of FIG. 8. FIG. 10 is an end view of a distal tip of the insertion tool 250. FIG. 11 is an end view of the proximal end of the insertion tool 250.

In the illustrated embodiment, the insertion tool 250 is configured to engage the second portion 234 of the anchor 230 to deliver or guide the anchor 230 into place within the body of the patient. The insertion tool 250 is configured to cause the second portion 234 of the anchor 230 to move with respect to the first portion 232 of the anchor 230. The insertion tool 250 may be used to place the second anchor 240 into the body of the patient.

The insertion tool 250 includes a handle portion 252 and a needle portion 254. The needle portion 254 has a tubular member 256 and a shaft or stylet 258. The tubular member 256 is coupled to the handle portion 252. The stylet 258 extends through a cavity or lumen defined by the tubular member 256. The stylet 258 has a proximal portion 261 that is disposed within the handle portion 252 and a distal portion 263 that disposed distally of the tubular member 256.

The needle portion 254 is sized and shaped to allow a user to position the implant 210 within the body of the patient. In the illustrated embodiment, the needle portion 254 includes a slight curvature. In other embodiments, the needle portion 254 includes a larger curvature. In yet other embodiments, the needle portion 254 is linear or substantially linear.

The stylet 258 is configured to rotate along a longitudinal axis with respect to the tubular member 256 and the handle portion 252. The stylet 258 is operatively coupled to an actuation member 259 that is disposed within a window or opening 257 defined by the handle portion 252 of the insertion tool 250. A user my grasp the handle portion 252 of the insertion tool 250 and move or rotate the actuation member 259 to rotate the stylet 258 with respect to the tubular member 256.

As best illustrated in FIG. 11, the actuation member 259 is disposed below the outer surface of the handle portion 252 of the insertion member 250. In use, a user inserts a finger or a portion of a finger into the opening defined by the handle portion 252 of the insertion tool 250 to access and move the actuation member 259 with respect to the handle portion 252. In some embodiments, this helps prevent unintentional movement of the actuation member 259. In other embodiments, the actuation member 259, or a portion of the actuation member 259, extends above an outer surface of the handle portion 252.

The distal tip 263 of the insertion tool 250 is configured to engage the anchors 230 and 240 to place or push the anchors 230 and 240 into place within the body of the patient. The distal tip 263 is "t" or star shaped. The distal tip 263 is configured to mate with and engage the recess 243 of the anchor 230. In some embodiments, the distal tip 263 is sized and shaped to frictionally couple (or operatively couple) within the recess 243 of the anchor 230.

When the distal tip 263 is engaged with the recess 243 of the anchor 230, the user of the insertion tool 250 (such as a physician) may rotate the actuation member 259 to rotate the stylet 258 and cause the second portion 234 of the anchor 230 to rotate with respect to the first portion 232 of the anchor 230. As the second portion 234 of the anchor 230 rotates with respect to the first portion 232 of the anchor 230, the second portion 234 of the anchor 230 will move longitudinally with respect to the first portion 232 of the anchor 230.

In embodiments where the implant 210 is being placed in a pelvic region of a female patient (for example, to be placed adjacent a bladder or bladder neck of a patient), a vaginal incision may be made and the implant 210 may be placed into the body of the patient through the vaginal incision. In some embodiments, the insertion tool 250 may be used to guide the implant 210 into the vaginal incision and to the appropriate location within the body of the patient.

For example, the insertion tool 250 may be used to insert and place the anchor 240 through the vaginal incision and into place within the body of the patient. The insertion tool 250 may then be engaged with the anchor (by inserting the tip of the insertion tool 250 into the recess of the anchor 230) and used to insert and place the anchor 230 through the vaginal incision and into place with the body of the patient. Once the anchor 230 is placed the support member may be placed below are proximate the portion of the body to be supported (such as a bladder or a urethera of a patient). To adjust the tension of the support member 220 against the portion of the body to be supported, the insertion tool 250 can be used to move the second portion 234 of the anchor 230 with respect to the first portion 232 of the anchor 230. Specifically, actuation member 259 may be rotated or moved by the user to move the second portion 234 of the anchor 230 with respect to the first portion of the anchor 230 (as described in detail above). As the support member 220 is coupled to the second portion 234 of the anchor 230, movement of the second portion 234 of the anchor 230 with respect to the first portion 232 of the anchor 230 will provide more tension (movement of the second portion 234 towards the first portion 232) or less tension (movement of the second portion 234 away from the first portion 232) on the support member 220. In other words, the movement of the second portion 234 with respect to the first portion 232 causes the operating length of the implant 210 to change.

Figure 12:
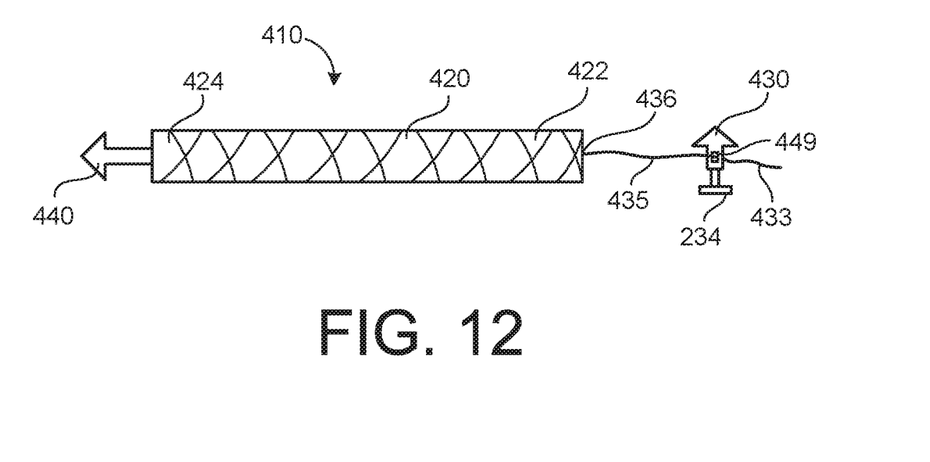
FIG. 12 is a top view of an implant according to an embodiment of the invention.

FIG. 12 is a top view of an implant 410 according to an embodiment. The implant 410 has a support member 420. The support member 420 includes a first end portion 422 coupled to a first mesh carrier or anchor 430 and a second end portion 424 coupled to a second mesh carrier or anchor 440.

The first end portion 422 is coupled to the first anchor 430 via a suture or tether 435. One end of the suture or tether 435 is coupled to the first end portion 422 of the implant 420. Any coupling method may be used to couple the end portion 436 of the suture or tether 435 to the first end portion 422 of the implant 420. For example, the suture or tether 435 may be tied or looped through a portion of the first end portion 422. In other embodiments, an adhesive may be used to couple the suture or tether 435 to the first end portion 422.

Figure 13:
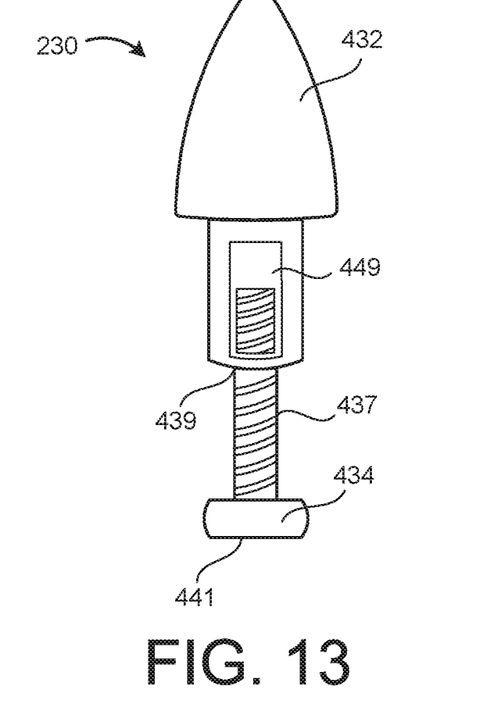
FIG. 13 is a side view of an anchor of the implant of FIG. 12.

The suture or tether 435 extends through an opening 449 defined by the anchor 430. FIG. 13 is a side view of the anchor 430. The opening 449 defines an axis that is offset from the longitudinal axis (or disposed at an angle with respect to the longitudinal axis) of the anchor 430. In the illustrated embodiment, the axis of the opening or lumen 449 is disposed orthogonally or perpendicularly to the longitudinal axis of the anchor 430. The anchor 430 includes a first portion 432 and a second portion 434. The second portion 434 of the anchor 430 is configured to move with respect to the first portion 432 of the anchor 430. In the illustrated embodiment, the second portion 434 of the anchor 430 moves with respect to the first portion 432 of the anchor 430 as a screw moves. The second portion 434 of the anchor 430 includes a ridge (a helical ridge) 437. The first portion 432 of the anchor 430 defines a lumen 439. The lumen 439 is configured to receive the first portion 432 of the anchor 430 and has a sidewall that defines a groove (a helical groove). The helical groove is configured to receive the helical ridge 437 of the second portion 434 of the anchor 430. The helical groove and the helical ridge 237 interact to selectively move the second portion 434 of the anchor 430 with respect to the first portion 432 of the anchor 430. Specifically, the second portion 434 of the anchor 430 may be rotated with respect to the first portion 432 of the anchor 430 to move the second portion 434 longitudinally with respect to the first portion 432 of the anchor 430.

In the illustrated embodiment, a proximal end 441 of the second portion 434 of the anchor 430 defines a recess or slot. The recess is configured to receive a portion of a delivery tool (such as delivery tool 250) to allow for the coupling or engaging of the delivery tool with the anchor 430 and to allow for the rotation of the second portion 434 of the anchor 430 with respect to the first portion 432 of the anchor 430.

The suture 435 extends through the opening 449 defined by the anchor 430. In the illustrated embodiment, the opening 449 is defined by the first portion 432 of the anchor 430. When the second portion 434 of the anchor 430 is in a first portion (as illustrated in FIG. 13), the suture 435 extends through the opening 449 and may move within the opening. Accordingly, the length of the implant between the anchors 430 and 440 may be adjusted by pulling the suture 435 through the opening 449 to a different location. The second portion 434 of the anchor 430 may be moved to a second position (toward the first portion 432 of the anchor 430) to lock the suture 435 in place with respect to the anchor 430. In the illustrated embodiment, the second portion 434 of the anchor 430 moves towards the first portion 432 of the anchor 430 to trap or frictionally engage or couple the suture 435 in place within the opening 449.

In use, the anchor 440 may be placed within the body of the patient. Anchor 430 may then be placed with the second portion 434 of the anchor 430 in its first position. The implant 420 may be positioned under a bodily portion to be supported (such as the bladder or bladder neck). The suture 435 may then be pulled or adjusted to move the suture 435 within the opening 449 of the anchor 440 and set the tension of the implant 410 and/or the length of the implant 410 between the anchors 430 and 440. Once the tension or length is set, the second portion 434 of the anchor 430 may be moved towards the first portion 432 of the anchor 430 to frictionally couple the suture 435 to the anchor 430.

In some embodiments, the suture 435 has a length sufficient to extend through the opening 449 and out of the body of the patient when the anchor 430 is placed within the body of the patient. For example, in some embodiments, the suture 435 has a length to extend from a vaginal incision of the patient when the anchor 430 is disposed within the body of the patient.

Figure 14:
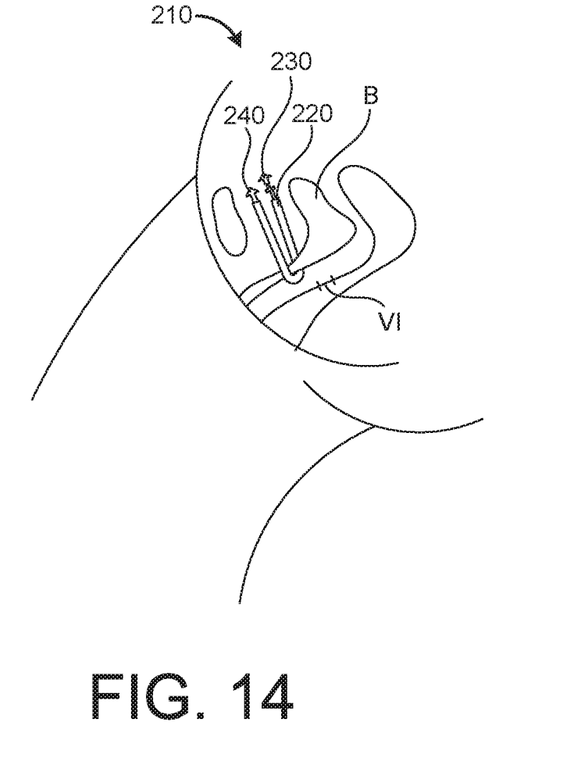
FIG. 14 is a schematic view of an implant disposed within a body of a patient.

FIG. 14 illustrates the implant 210 disposed within a pelvic region of a female patient. The support member 220 is disposed adjacent a portion of a bladder B of the patient and the anchors 230 and 240 are disposed in pelvic tissue.

Figure 15:
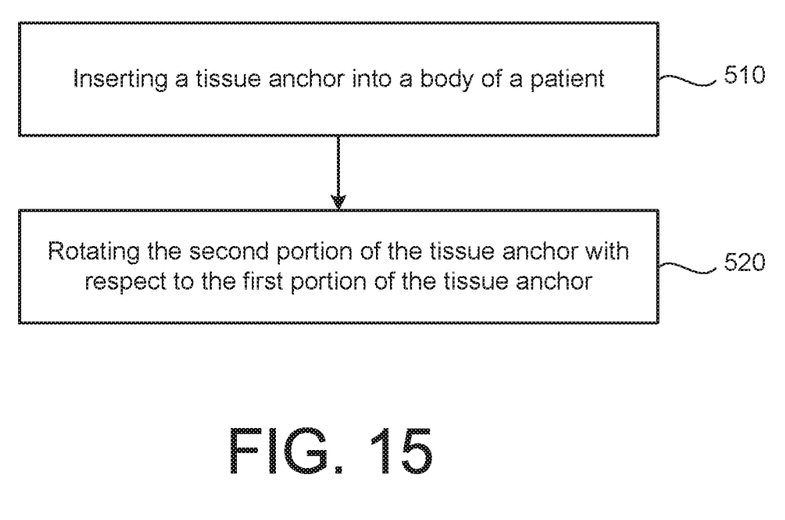
FIG. 15 is a flow chart of a method according to an embodiment of the invention.

FIG. 15 is a flow chart of a method 500 according to an embodiment. The method includes at 510 inserting a tissue anchor into a body of a patient. The tissue anchor includes a first portion and a second portion that is configured to move with respect to the first portion. At 520, the second portion of the tissue anchor is adjusted with respect to the first portion of the tissue anchor. For example, in some embodiments, the second portion of the tissue anchor is rotated with respect to the first portion of the tissue anchor. In some embodiments, the rotation of the second portion of the tissue anchor with respect to the first portion of the tissue anchor includes engaging a shaft or a stylet with the second portion of the tissue anchor. In some embodiments, the shaft or stylet is engaged with the second portion of the tissue anchor by inserting a tip or end portion of the shaft or stylet into a recess or slot defined by the second portion of the tissue anchor.

In some embodiments, the method 500 includes inserting a second tissue anchor into the body of the patient. A sling or support member extends from the first tissue anchor to the second tissue anchor.

In some embodiments, a medical device includes a tissue anchor having a first portion and a second portion. The tissue anchor is configured to be placed within bodily tissue of a patient. The first portion of the tissue anchor includes an extension member configured to engage the bodily tissue to help retain the tissue anchor within the bodily tissue. The first portion has an inner surface and defining a cavity. The second portion of the tissue anchor has a helical ridge. The helical ridge is configured to engage the inner surface of the first portion of the tissue anchor to movably couple the second portion of the tissue anchor to the first portion of the tissue anchor.

In some embodiments, the extension member is a barb member. In some embodiments, the inner surface of the first portion defines a helical groove. The helical ridge of the second portion of the tissue anchor is configured to engage the helical groove of the inner surface of the second portion of the tissue anchor.

In some embodiments, the medical device includes an implant coupled to the tissue anchor.

In some embodiments, the tissue anchor is a first tissue anchor and the device further includes an implant having a first end portion and a second end portion opposite the first end portion. The first end portion is coupled to the first tissue anchor. The second end portion is coupled to a second tissue anchor. In some embodiments, the second portion of the tissue anchor is configured to rotate with respect to first portion of the tissue anchor. In some embodiments, the second portion of the tissue anchor includes an engagement portion configured to engage an insertion device. In some embodiments, the second portion of the tissue anchor includes a slot configured to engage an insertion device. In some embodiments, the first portion of the tissue anchor defines a longitudinal axis. The first portion of the tissue anchor defines a lumen defining a longitudinal axis. The longitudinal axis of the first portion of the tissue anchor is offset from the longitudinal axis of the lumen.

In some embodiments, the first portion of the tissue anchor defines a longitudinal axis. The first portion of the tissue anchor defines a lumen defines a longitudinal axis. The longitudinal axis of the first portion of the tissue anchor is disposed at an angle with respect to the longitudinal axis of the lumen.

In some embodiments, a medical device includes an elongate member having a proximal end portion and a distal end portion, a shaft member, and an actuator. The elongate member defines a cavity. The shaft member is at least partially disposed within the cavity of the elongate member. The shaft member is configured to rotate with respect to the elongate member. The actuator is operatively coupled to the shaft member and configured to cause the shaft member to rotate with respect to the elongate member.

In some embodiments, a portion of the shaft member extends from the distal end portion of the elongate member. In some embodiments, a portion of the shaft member extends from the distal end portion of the elongate member and a portion of the actuator extends from a sidewall of the proximal end portion. In some embodiments, the actuator is configured to rotate with respect to the elongate member. In some embodiments, the actuator is configured to rotate with respect to the elongate member and at least a portion of the actuator extends from a sidewall of the proximal end portion. In some embodiments, the shaft member includes a tip that is configured to engage a tissue anchor.

In some embodiments, a method of placing a medical device within a body of a patient includes inserting a tissue anchor into the body of the patient, the tissue anchor having a first portion and second portion; and adjusting the second portion of the tissue anchor with respect to the first portion of the tissue anchor.

In some embodiments, the adjusting is a rotating and the rotating the second portion of the tissue anchor with respect to the first portion of the tissue anchor includes engaging the second portion of the tissue anchor with an insertion device that includes a shaft that is rotatably disposed within a cavity of an elongate member. In some embodiments, the rotating the second portion of the tissue anchor with respect to the first portion of the tissue anchor includes engaging a projection of a shaft of an insertion device with a slot defined by the second portion of the tissue anchor. In some embodiments, the tissue anchor is a first tissue anchor and the method further includes inserting a second tissue anchor into the body of the patient, the second tissue anchor being coupled to a sling member.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method of placing a medical device within a body of a patient, comprising:
   making a vaginal incision in the body of the patient;
   inserting, via the vaginal incision, the medical device in a pelvic floor region of the patient, the inserting the medical device including:
      inserting a first tissue anchor into a first portion of a pelvic tissue of the patient, the first tissue anchor being directly coupled with a first end of a support member of the medical device;
      inserting a second tissue anchor into a second portion of the pelvic tissue of the patient, the second tissue anchor being directly coupled with a second end of the support member of the medical device, the second tissue anchor having a first member and second member, the first member having an extending portion, the extending portion defining a lumen that is configured to receive the second member, the extending portion having a first diameter, and a lead portion of the first member having a second diameter, the second diameter being larger than the first diameter; and
   adjusting tension of the support member of the medical device on a portion of the body of the patient by adjusting a position of the second member of the second tissue anchor with respect to a position of the first member of the second tissue anchor.

2. The method of claim 1, wherein the adjusting the position of the second member of the second tissue anchor with respect to the position of the first member of the second tissue anchor includes rotating the second member of the second tissue anchor by engaging the second member of the second tissue anchor with an insertion device that includes a shaft that is rotatably disposed within a cavity of an elongate member.

3. The method of claim 1, wherein the adjusting the position of the second member of the second tissue anchor with respect to the position of the first member of the second tissue anchor includes rotating the second member of the second tissue anchor by engaging a projection of a shaft of an insertion device with a slot defined by the second member of the second tissue anchor.

4. The method of claim 1, wherein the first tissue anchor is a one part tissue anchor.

5. The method of claim 1, wherein adjusting tension of the support member of the medical device on a portion of the body of the patient includes adjusting tension of the support member against one of a bladder, a bladder neck or a urethra of the patient.

* * * * *